United States Patent [19]

Lowry et al.

[11] 4,272,986
[45] Jun. 16, 1981

[54] METHOD AND MEANS FOR MEASURING MOISTURE CONTENT OF HERMETIC SEMICONDUCTOR DEVICES

[75] Inventors: Robert K. Lowry, Melbourne Beach; Larry A. Miller, Palm Bay, both of Fla.

[73] Assignee: Harris Corporation, Melbourne, Fla.

[21] Appl. No.: 30,498

[22] Filed: Apr. 16, 1979

[51] Int. Cl.³ .............................................. G01N 27/18
[52] U.S. Cl. ...................................... 73/73; 324/65 R; 338/35; 357/75
[58] Field of Search ............... 73/73, 29, 335; 338/35; 324/65 R; 357/75; 200/61.06

[56] References Cited

U.S. PATENT DOCUMENTS

| 3,890,703 | 6/1975 | Frazee et al. | 338/35 X |
| 3,943,557 | 3/1976 | Frazee et al. | 357/75 |
| 4,050,048 | 9/1977 | Frazee et al. | 338/35 |
| 4,057,823 | 11/1977 | Burkhardt et al. | 357/75 X |
| 4,143,177 | 3/1979 | Kovac et al. | 338/35 X |

FOREIGN PATENT DOCUMENTS 2702487 7/1977 Fed. Rep. of Germany ............ 73/335

OTHER PUBLICATIONS

Merrett, R. P. et al., *Moisture Measurement Technology for Hermetic Semiconductor Devices*, In ARPA/NBS Workshop, Mar. 22-23, 1978, pp. 27-28.
Meyer, D. E., *Miniature Moisture Sensors for In-Package Use by the Microelectronics Industry*, pp. 48-52.

*Primary Examiner*—Gerald Goldberg
*Assistant Examiner*—Joseph W. Roskos
*Attorney, Agent, or Firm*—Leitner, Palan, Martin & Bernstein

[57] ABSTRACT

The moisture content of a hermetically sealed semiconductor device is a function of the dew point of the cavity atmosphere which is the temperature of maximum surface conductivity. A pattern of interdigitated thin film aluminum conductors is provided on an impurity free, non-porous silicon oxide insulative substrate. The surface conductivity of this structure rises as moisture condenses onto and between the conductors as the temperature is reduced at a slow controlled rate to the dew point temperature. The amplitude of the maximum surface conductivity is proportional to ionic impurity concentration.

23 Claims, 4 Drawing Figures

NOMOGRAPH FOR DEWPOINTS AND PPM AS A FUNCTION OF P

METHOD AND MEANS FOR MEASURING MOISTURE CONTENT OF HERMETIC SEMICONDUCTOR DEVICES

BACKGROUND OF THE INVENTION

1. Field of the Invention

The present invention relates generally to moisture detectors, and more specifically to a moisture content detector for a hermetically sealed semiconductor device.

2. Description of the Prior Art

Moisture within hermetic packages may cause premature device failure due to electrogalvanic corrosion of chip metallization. Knowledge of package moisture contents thus becomes a critical parameter both for operating reliability as well as process technology improvements and quality control.

Mass spectroscopy has been the definitive method for measuring package moisture. It is relatively expensive to either acquire the instrumentation or for per-sample charges by service laboratories. The test is destructive to the sample package and if not executed carefully, it can also be destructive to the encapsulated device precluding further failure analysis. Results are not obtainable at the time that the need for them arises.

An in-situ monitor, in which a sensing device is mounted directly in a sample package, or incorporated into the design of a circuit, offers rapid availability of moisture data. Analysis cost per sample is inexpensive, only about 10% of the cost of a mass spectrometer analysis. This means that statistically significant numbers of packages can be analyzed on a more frequent basis. The in-situ monitor thus enables more exacting process development experimentation and process control measurements, and speeds up vendor and assembly lot qualifications. Moreover, the in-cavity sensor gives a real-time dynamic analysis of moisture within a package. The determination can be made repeatedly so that moisture conditions can be monitored as a function of part storage or operating lifetime.

Two classes of in-situ sensors for integrated circuit packages have been developed. The first is the surface conductivity sensors and the second is the volume effect sensors. The surface conductivity sensors are those which measure the conductivity of moisture condensed on a non-porous surface between two spaced electrodes using a "dew point test". The volume effect sensor measures the conductivity of a porous surface which absorbs moisture. In an experiment, reported by D. E. Meyer in "Miniature Moisture Sensors For In Package Use By The Microelectronics Industry", Reliability Physics Symposium, Las Vegas, Nevada April 1975, an $Al_2O_3$ volume effect sensor was tested with a fired thick film interdigitated surface conductivity sensor and an interdigitated thin aluminum film on oxidized silicon dew point-resistivity sensor. The thick film sensor did not provide sensitivity below 10,000 ppmv. The dew point-resistance sensor did not provide repeatable results, which was attributed to the moisture selectively condensing on the package surface instead of on the sensor. The study concludes that $Al_2O_3$ volume effect sensors are far superior, although they cannot withstand elevated package sealing temperatures. Thus these two surfaces conductivity sensors were abandoned and industry directed their efforts to the volume effect sensors.

There are many examples of the volume effect sensors used as humidity sensors in hermetically sealed integrated circuit packages. U.S. Pat. Nos. 3,943,557 and 4,050,048 to Frazee discuss the use of cobalt oxide as a hygroscopic media formed on a surface of the package to detect the percentage of humidity in the package.

The formation of a moisture sensor on an integrated circuit wherein selected portions of the silicon chip are made porous by an anodic etching and a pair of aluminum conductors is formed above the porous area as described in U.S. Pat. No. 4,057,823 to Burkhardt, et al. In each of these patents, the relative humidity is determined by measuring changes in the resistance or the capacitance of the porous structure when water molecules diffuse therein.

These devices illustrated in these patents require special material, for example, cobalt oxide or other moisture sensitive oxide complexes or may include additional steps for preparing a hygroscopic surface. Similarly, almost all these detectors measure the change in resistance or capacitance of the hygroscopic surface to indicate relative humidity. While such sensors are useful for low-temperature sealed packages, their fragile $Al_2O_3$ structure does not withstand elevated temperatures and they are not suitable for solder glass sealed ceramic packages.

Another type of moisture detector was presented by R. P. Merrett and S. P. Sim at the ARPA/NBS workshop, National Bureau of Standards, Mar. 22-23, 1978 in a talk entitled "Assessment Of The Use Of Measurement Of Surface Conductivity As A Means Of Determining Moisture Contents Of Hermetic Semiconductor Encapsulations". Although the conductors were formed on a nonporous $SiO_2$ surface, the measurement of the $SiO_2$ surface conductivity was utilized in a "dew-point test" by using the field effect structure to detect the changing of the surface of the oxide surrounding a biased electrode.

Although knowledge of the relative humidity of a hermetically sealed package or a humid environment may be desirable, the prior art has not directed itself to detecting the moisture content in parts per million by volume of hermetically sealed semiconductor package or other sealed environments. In light of the new government specification requirements for limitation of moisture contents of hermetic devices, to below 10,000 ppm per volume namely MIL-STD-883B, method 1018, an in-situ sensor is desirable for determining the water content of hermetically sealed devices to below 10,000 ppm by volume.

SUMMARY OF THE INVENTION

The present invention measures the amount of moisture in a hermetically sealed environment by determining the dew point in the environment and calculating therefrom the amount of moisture in parts per million by volume. The dew point of the sealed atmosphere is determined by lowering the temperature of the cavity at a slow, controlled rate of no greater than 15° C. per minute while the surface conductivity of the conductor pattern of the sensor is monitored. As the dew point temperature of the cavity environment is approached, micro-droplets of water will condense on the surface of this sensor. The dew point and consequently the maximum conductivity occurs when all water molecules available have condensed out of the cavity environment. The temperature at the maximum surface conductivity is used to calculate the moisture content as parts per million. The amplitude of the conductivity peak is proportional to ionic impurities concentration.

The surface conductivity is measured by providing thin film aluminum conductors having a thickness no greater than 12,000 angstroms inter-digitized within spacing of no greater than 0.5 mils on a silicon oxide surface. The silicon oxide is substantially non-porous and impurity free such that the surface conductivity between the aluminum conductors is a function of the amount of condensed moisture and does not reflect moisture absored into the surface of the oxide nor the surface conduction produced by impurities in the oxide. Aluminum conductors on silicon oxide surfaces are not affected by the high sealing temperatures for ceramic packages.

OBJECTS OF THE INVENTION

An object of the present invention is to provide an in-situ measurement of moisture content of a hermetically sealed package.

Another object of the invention is to provide a moisture content measuring device in hermetically sealed package which requires common material and processing steps.

A further object of the present invention is to provide a method for determining moisture content of a hermetically sealed package which may be performed in the manufacturing plant without submission to outside laboratories.

Still another object of the present invention is to provide a moisture sensor which is not affected by the high sealing temperatures of ceramic hermetically sealable packages.

An even further object of the present invention is to provide a method of measuring moisture and ionic impurity content of a hermetically sealed package.

A still further object of the present invention is to provide a surface conductivity sensor capable of accurately measuring moisture in a hermetically sealed packeage below 10,000 ppmv.

Other objects, advantages and novel features of the present invention will become apparent from the following detailed description of the invention when considered in conjunction with the accompanying drawings.

DESCRIPTION OF THE PREFERRED EMODIMENTS

Figure 1:
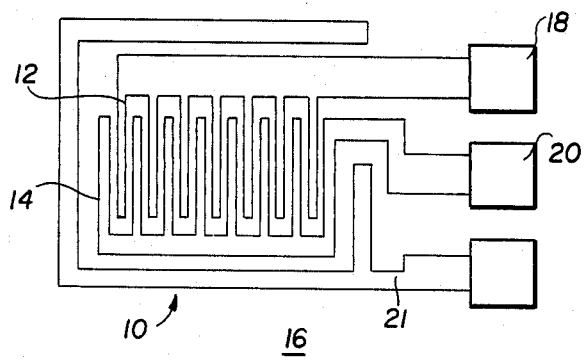
FIG. 1 is a plan view of a sensor incorporating the principles of the present invention.

The method of the present invention recognizes the principle that the dew point of a sealed atmosphere will vary with the moisture content of the atmosphere. Similarly, the dew point and moisture content of the sealed atmosphere will vary with pressure of the sealed atmosphere. Thus, knowing the pressure and the dew point, the moisture content of a sealed atmosphere may be determined. To measure the dew point of a sealed atmosphere, the atmosphere may be heated at a temperature and for a period sufficient to varporize all the moisture in the cavity defining the sealed atmosphere and desorb water molecules from the walls of the cavity. This temperature is generally 100° C. The temperature is then lowered at a slow, controlled rate while the electrical conductivity of the surface conductivity detector is monitored. The surface conductivity rises as the lowering temperature approaches the dew point until the condensed water ceases forming on the sensor surface. The temperature at which the maximum conductivity occurs is the point at which all available water molecules have condensed out of the cavity atmosphere and represents the dew point of the atmosphere. From the gas pressure within the cavity and the dew point temperature, the water vapor content in parts per million by volume may be calculated.

Since the method of the present invention measures the surface conductivity for varying temperatures to determine the maximum conductivity produced by condensation of water molecules, it is important that the surface conductivty is limited to the condensed water molecules between the electrodes on the substrate and not on the moisture content or surface conductivity of the substrate. As reported by Robert B. Comizzoli at pages 386–391 of the March 1976 Journal of the Electrochemical Society, in an article titled, "Bulk and Surface Conduction and CVD, $SiO_2$, and PSG Passive Layers", the conductivity of these insulated layers varies as a function of time and phosphorus content. The bulk conductivity, namely vertical conductivity through the layer of silicon dioxide is greater than that for phosphosilicate glass (PSG). This is related to the ability of the sodium ions to conduct current in the phosphorus free silicon oxide. After exposure to humidity, the bulk conductivity of the PSG is greater than that of the phosphorus free silicon oxide. These results are accounted for by the water penetration in the glass surface of the PSG and its lateral diffusion under the metal electrodes. The surface conductivity of phosphorus free silicon oxide is higher than that of the PSG below 70% humidity and above which the samples vary.

The moisture absorption ability of glasses increase with phosphorus and phosphorus oxide. A layer of phosphosilicate glass (PSG) has even been used as a moisture detector. In an investigation of aluminum corrosion, W. M. Paulson and R. W. Kirk ("The Effect of Phosphorus-doped Passivation Glass on the Corrosion of Aluminum," Proceeding of the Twelfth Annual Reliability Physics Symposium, 1974, pages 172–179) reported that the magnitude of ionic current flow between two surface electrodes through the surface of the glass is a function of the amount of water absorbed, the glass surface and its interaction with the water, and any ions on the surface.

The data of the study indicates that the surface conductivity varies as a function of the insulative layer surface method of preparation as well as composition including impurities. Thus, to minimize any side effect or undesirable conductivity between the electrodes which would reflect impurity concentration, for example, dopant impurities or impurities produced during processing, for example, sodium, the oxide layer must be produced by a method which minimizesthese effects. Therefore, it is suggested that the oxide layer be thermally grown versus chemically vapor disposed. This reduces the formation of sodium impurities. By reducing the impurities the conduction between the electrodes on the surface of the insulative layer will reflect only the condensed moisture between the layers and not the impurities of or the absorption rate into the insulative layer.

Such a sensor is illustrated in FIG. 1 as 10 including a pair of interdigitized conductor strips 12 and 14 formed on a thermally grown oxide layer 16 and including contact pads 18 and 20. A guard ring conductor 21 may also be provided. The device may be formed during normal processing of integrated circuit devices wherein the oxide layer 16 is a thermally grown silicon dioxide on a silicon substrate and the conductor strips 12 and 14 are formed from a layer of aluminum applied and delineated using a photolithographic technique. Thus, the device is compatible with the processing steps and may be processed simultaneously with the formation of other semiconductor devices in a silicon substrate.

The sensor may be formed in a space of 5+8 mils wherein the fingers have a thickness of approximately 8,000 to 10,000 angstroms and a separation of approximately 0.2 to 0.3 mils. The thickness should not exceed approximately 12,000 angstroms and the separation should not exceed approximately 0.5 mils. As noted in the Meyer article, prior art thick film surface conductivity devices were not sensitive enough to detect moisture concentration of less than 10,000 ppm because of the large resistance and capacitance of the thick film sensors. The present sensor is a thin film sensor which improves electrical sensitivity by minimizing the resistance of the interdigitized conductors. The ability of the present sensor to measure accurately under 10,000 ppm results from limiting the separation of the interdigitized sensor conductors to below approximately 0.5 mils. This assures that the small amounts of the droplets present will be detected. These are but an example of the physical dimensions of which detector 10 may be formed.

The sensor 10 may be part of an intergrated circuit or may be formed separately and mounted in a sealed package with other integrated circuits. The bottom pads 18 and 20 are connected to metallic leads extending from within the cavity to the exterior of the housing. The packaging having a cavity therein may include metal as well as ceramic housings. By using field oxide or silicon dioxide and aluminum conductive strips, the sensor is not degraded during the high sealing temperatures of ceramic packages. Since these temperatures can exceed 500° C., other types of moisture detectors are deleteriously affected at such high temperatures. Although the sensor 10 of FIG. 1 is described as being formed on the surface of a substrate integrated circuit, it may also be formed or mounted to any portion of the interior cavity. Other materials which may form the non-porous layer and are unaffected by the 500° C. sealing temperature are silicon nitride. The conductive strips 12 and 14 may be formed of aluminum, gold or any similar conductive metal.

Figure 2:
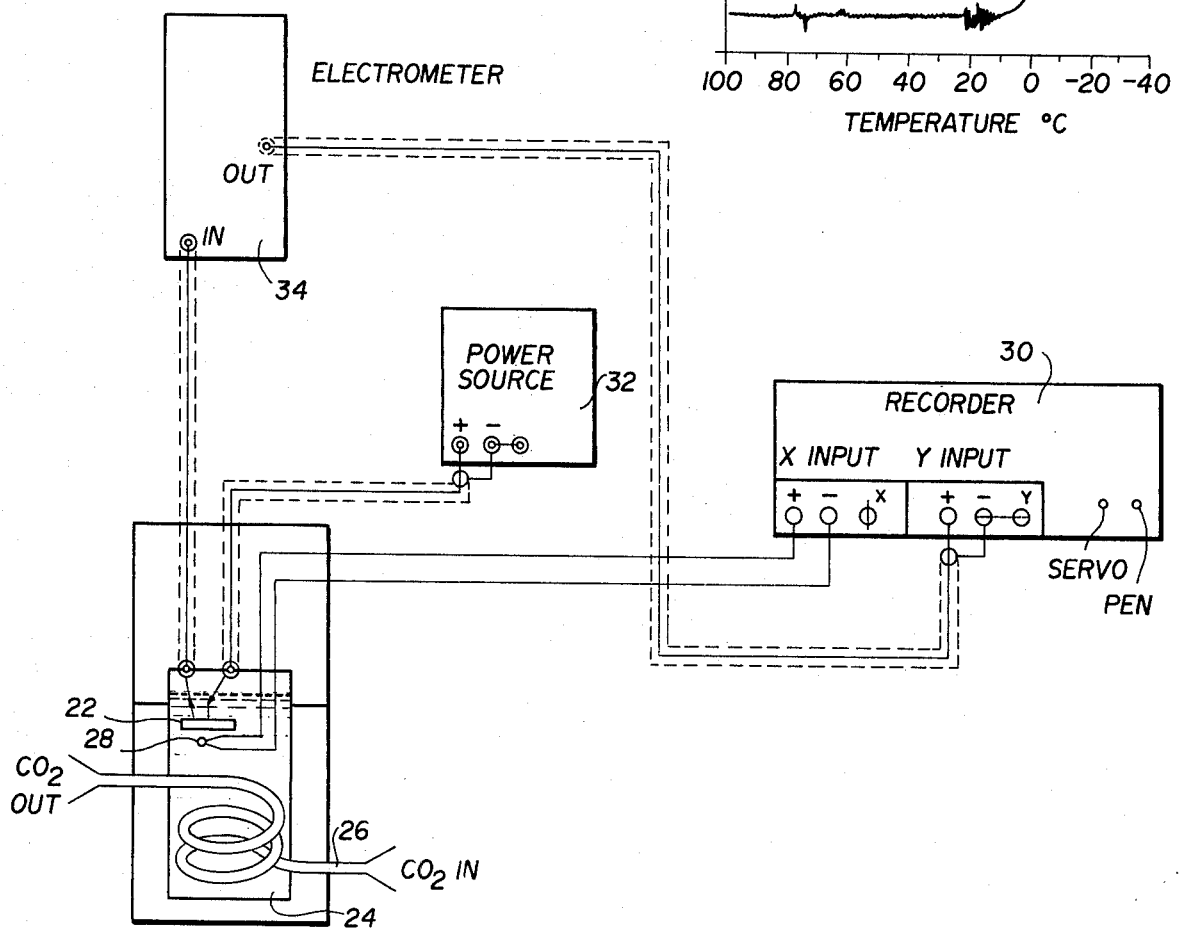
FIG. 2 is a block diagram of the apparatus used to practice the method of the present invention.

A hermetically sealed package having integrated devices therein and the sensor 10 of FIG. 1 was tested using the method of the present invention to determine the moisture content in parts per million by volume as illustrated in FIG. 2. The package 22 is inserted in a bath 24 of a dielectric fluid wherein it is heated. An example of a dielectric fluid would be a silicone oil, for example, Dow Corning 200. The bath 24 is first heated by an immersion element and then cooled by a gas transmitted through coil 26. The temperature of bath 24 is monitored by a sensor 28 which may be a thermocouple which is connected to the one input, for example, an X input of a recorder 30. The surface conductivity between the conductor strips 12 and 14 is monitored by applying a DC voltage from power source 32 across the leads and the resulting current being monitored by an electrometer 34 which may be, for example, a Keithley electrometer. The output of the electrometer 34 is connected to the Y input of the recorder 30 which includes a pen and strip chart.

The method of the present invention begins with heating the liquid 24 to a sufficient temperature, for example, 100° C., to ensure all the water molecules within the cavity of the package 22 are desorbed from the walls of the cavity and are vaporized. The temperature is then lowered at a slow, controlled rate of, for example, 10° C., per minute by transmitting $CO_2$ through coil 26 at a very slow rate while the electroconductivity of the conductor strips 12 and 14 is monitored by the electrometer 34. The temperature and conductivity are recorded by recorder 30. As the dew point temperature of the package 22 cavity is approached, microdroplets of water will begin to condense on the surface of the sensor 10. The droplets cumulatively bridge the conductive strips 12 and 14, thereby providing multiple current paths, and the conductivity of the sensor 22 rises accordingly. The conductivity rises until condensed water ceases forming on the sensor surface. The temperature at which the maximum conductivity occurs is the point at which all available water molecules have condensed out of the cavity atmosphere and therefore represents the dew point.

Figure 3:
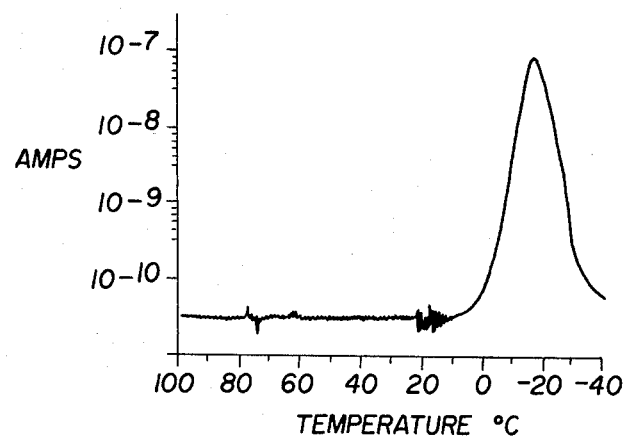
FIG. 3 is a graph of surface conductivity versus temperature reulting from the method of the present invention.
Figure 4:
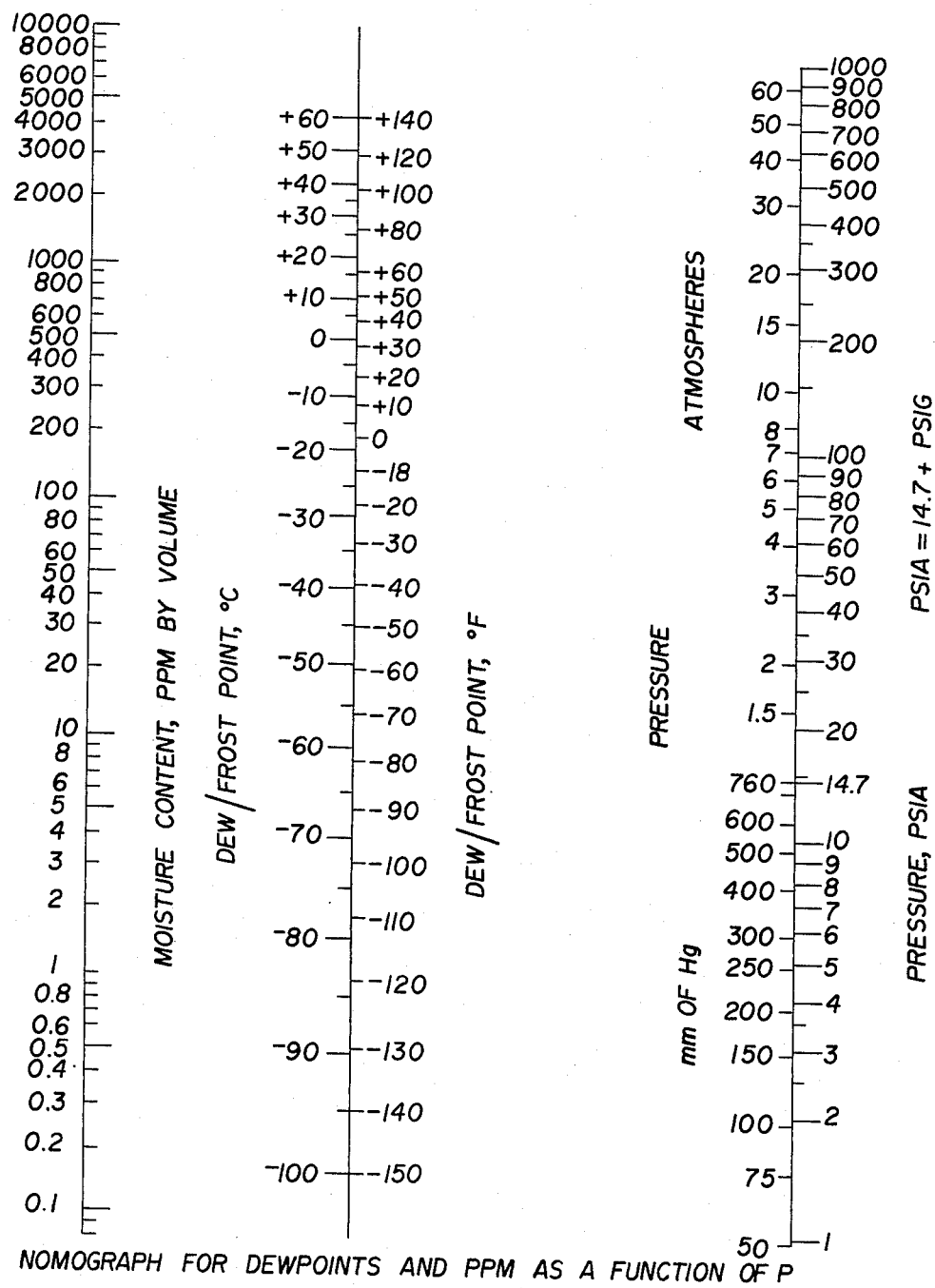
FIG. 4 is a nomograph of dew point and moisture content as a function of pressure.

A chart from recorder 30 showing the results of one test is illustrated in FIG. 3 as a plot of temperature in degrees centigrade versus conductivity in nanoamperes. A sharp peak or maximum conductivity occured at approximately −12° C., A nomograph, for example, that of FIG. 4 was used to convert the dew point temperature with an adjustment for pressure to moisture content in parts per million by volume. Since the package whose test is reflected in FIG. 3 was a ceramic housing sealed at approximately 440° C., at one atmosphere, the pressure at the dew point or an ambient temperature using Gay-Lussac's Law (P T, V constant) is approximately a half an atmosphere. Using half an atmosphere at −12° C., the nomogram of FIG. 4 calculates a water content of 4200 parts per million by volume. The relationship of dew point and moisture content are a function of pressure.

Since the method of calculating moisture content does not involve an absorption surface whose resistivity is measured as a reflection of humidity but instead merely measures the condensation of liquid between two conductors on a non-porous insulative surface, the sensor need not be formed of any special materials and may be formed as part of a standard integrated circuit process. The sensor 10 is considered a dew point sensor which is related to and facilitates the determination or calculation of the moisture content. The sensor 10 is not degraded by the high sealing temperatures of ceramic housings. It was noticed during experimentation that with metal housings, the metal walls formed condensing surfaces which preferentially attracted condensed water molecules since the walls cooled more rapidly than the sensor to yield falsely low readings. Thus, if the process is going to be used with metal housings, the metal housing must be coated with an insulative material, for example, RTV silicone. This prevents the condensation at the metal walls and allows the condensation to occur on the sensor 10 to provide more accurate results. Also, the use of liquid nitrogen as the cooling fluid in coil 26 caused the package to cool too rapidly. This caused condensation on the package surface even in ceramic packages. Thus it is critical that the temperature be lowered at a slow controlled rate no greater than 15° C. per minute. This will prevent the moisture from selectively condensing on the package surface. Although $CO_2$ was described as the cooling gas other coolants for example freon may be used.

Although the method described and illustrated in FIGS. 2 and 3 began with heating the packages to vaporize all the moisture in the cavity including desorption of moisture from the cavity walls, this preheating may be eliminated in some cases. Experiments on ceramic packages using initial temperature values from 25° C. to 125° C. at the start of the cool down cycle show that regardless of initial temperature used, the maximum conductivity of the specimen's sensor always corresponded to the same water content. Even at 125° C., no additional water was desorbed to the cavity ambient. This suggests that cycling of a hermetic specimen higher than room temperature is not necessary to assure that all available water within the cavity will condense onto the sensor. For substantially high moisture, preheating the moisture of the package atmosphere is needed for accurate measurements. If it is desired only to determine whether the moisture is below for example 10,000 ppmv, the preheating can be eliminated.

The surface conductivity sensor also provides information about cleanliness of the sealed package cavity. Amplitude of the current peak (of FIG. 3 for example) is independent of the quantity of water in the package, but will vary according to concentrations of dissolved ions.

Experiments show that peak amplitudes are typically $10^{-9}$ to $10^{-7}$ amperes for Cerdips sealed with vitreous glasses and $10^{-7}$ to $10^{-5}$ amperes for Cerdips sealed with devitrifying glasses. These magnitudes are obtained reproducibly, regardless of the actual quantity of water within the package. Experiments confirm that current magnitude of the sensor is directly proportional to numbers of ions in the condensed water. It is concluded that quantities of ions are leached from internal surfaces of the package by water vapor and transferred to the sensor surface dissolved in the condensate. The sensor curves therefore provide at least a first-order approximation of cleanliness of the package materials.

From the preceding description of the preferred embodiment, it is evident that the objects of the invention are attained in that a method and sensor are provided which allows in-situ measurement of moisture content by monitoring the surface conductivity to determine dew point. Although the invention has been described and illustrated in detail, it is clearly understood that the same is by way of illustration and example only and is not to be taken by way of limitation. The specific sensor described is insensitive to the high sealing temperatures of ceramic housings and can be formed inexpensively using standard techniques. The spirit and scope of this invention is to be limited only by the terms of the appended claims.

What is claimed:

1. A method of measuring the amount of moisture in a hermetically sealed semiconductor device package comprising:
providing parallel conductive elements having a thickness no greater than 12,000 angstroms and a separation of no greater than 0.5 mils on an insulative surface is said package;
simultaneously lowering the temperature of said package at a rate no greater than 15° centigrade per minute to condense the water vapor and measuring the conductivity between said conductive elements; and
determining the moisture content from the temperature of maximum conductivity.

2. The method of claim 2 wherein providing said conductive strips includes forming interdigitized aluminum conductive strips on a substantially impurity free, substantially non-porous, insulative surface in said package.

3. The method of claim 2 wherein said package is heated at a temperature in the range of 100° Centigrade prior to lowering the temperature.

4. The method of claim 1 wherein said package includes metallic portions and including the step of insulating said metallic portions to prevent condensation on the metallic surfaces.

5. The method of claim 1 wherein said temperature is lowered at a rate of 10 degrees centigrade per minute.

6. The method of claim 1 wherein said conductive strips are formed on a non-porous, thermal grown insulative surface of a semiconductor substrate.

7. A method of measuring dew point of the atmosphere in a sealed cavity comprising:
providing a surface conductivity sensor in a sealed cavity having parallel conductors of a thickness no greater than 12,000 angstroms and a separation of no greater than 0.5 mils on a non-porous insulative surface; and
simultaneously lowering the temperature in said cavity at a rate no greater than 15° centigrade per minute to determine dew point as the temperature of maximum conductivity and measuring the conductivity of liquid condensed on said surface between said conductors.

8. The method of measuring dew point according to claim 7 wherein said sealed cavity is formed by a ceramic housing hermetically sealed and said surface is substantially impurity free silicon oxide surface and said conductors are aluminum.

9. A method of measuring the concentration of dissolved ions in the atmosphere of a hermetically sealed semiconductor device package comprising:
providing a surface conductivity sensor on a non-porous surface in said sealed cavity;
heating said cavity at a temperature sufficient to vaporize the moisture in said cavity;
simultaneously lowering the temperature in said cavity and measuring the surface conductivity of liquid condensed on said sensor; and
determining the approximate concentration of dissolved ions from the magnitude of the point of maximum surface conductivity.

10. The method of measuring concentration of dissolved ions according to claim 9 wherein said sensor includes a pair of interdigitized conductors having a thickness no greater than 12,000 angstroms and a separation of no greater than 0.5 mils.

11. The method of measuring concentration of dissolved ions according to claim 9 wherein said heating is to a temperature in the range of 100° centigrade and lowered at a rate no greater than 15° centigrade per minute.

12. A hermetically sealed package including a semiconductive device and an integral moisture detector comprising:
   means forming a cavity for retaining said semiconductive device;
   means hermetically sealing said cavity;
   a plurality of metallic leads extending from within said cavity to the outside of said package;
   a non-porous insulative oxide layer in said package;
   exposed parallel conductors having thickness no greater than 12,000 angstroms and a separation of no greater than 0.5 mils formed on said oxide layer; and
   electrodes connecting said conductors to a pair of said leads whereby the moisture content of the sealed package may be determined by monitoring the conductivity of liquid condensed on the surface between said conductors in the temperature region of the dew point of the cavity atmosphere.

13. The hermetically-sealed package according to claim 12 wherein said oxide layer is a substantially impurity free, substantially non-porous silicon oxide and said conductors are interdigitated aluminum.

14. The hermetically-sealed package according to claim 12 wherein said means forming said cavity is a ceramic material.

15. In a hermetically-sealed package including a semiconductor device in a sealed cavity of said device package, the improvement comprising means in said cavity for facilitating the measurement of dew point for the atmosphere in the sealed cavity, said means including parallel conductor means formed having a thickness no greater than 12,000 angstroms and a separation of no greater than 0.5 mils on a non-porous, thermally grown insulative surface in said sealed cavity for detecting the presence of condensed moisture on said insulative surface between said conductor means.

16. The hermetically-sealed package according to claim 15 wherein said insulative surface is an oxide layer of said semiconductor device.

17. The hermetically-sealed package according to claim 16 wherein said oxide layer is a substantially impurity free, substantially non-porous silicon oxide and said conductors are aluminum.

18. The hermetically-sealed package according to claim 15 wherein said package is of a ceramic material.

19. In a hermetically sealed package including a semiconductor device in a sealed cavity of said package, the improvement comprising means in said cavity for facilitating the measurement of concentration of dissolved ions in the atmosphere in the sealed cavity, said means including a pair of parallel conductor means formed on a non-porous insulative surface in said sealed cavity for detecting the dissolved ion concentration of the liquid condensed onto said insulative surface between said pair of conductor means.

20. The hermetically sealed package according to claim 19 wherein said conductor means have a thickness not exceeding 12,000 angstrom and a separation not exceeding 0.5 mils.

21. A surface conductivity moisture sensor comprising a non-porous, impurity free insulative surface on a substrate and interdigitized metallic conductors having a thickness no greater than 12,000 angstroms and a separation of no greater than 0.5 mil for detecting condensed moisture on said insulative surface between said conductors.

22. The surface conductivity moisture sensor according to claim 21 wherein said insulative surface is thermal grown silicon oxide.

23. The surface conductivity moisture sensor according to claim 21 wherein said conductors are aluminum.

* * * * *

UNITED STATES PATENT AND TRADEMARK OFFICE
CERTIFICATE OF CORRECTION

PATENT NO. : 4,272,986
DATED : June 16, 1981
INVENTOR(S) : Robert K. Lowry and Larry A. Miller It is certified that error appears in the above—identified patent and that said Letters Patent is hereby corrected as shown below:

Column 4

Line 64, delete "minimizesthese" and insert --minimizes these--

Column 5

Line 19, delete "5 + 8" and insert --5 x 8--

Signed and Sealed this

Twenty-seventh Day of October 1981

[SEAL]

Attest:

GERALD J. MOSSINGHOFF

*Attesting Officer*   *Commissioner of Patents and Trademarks*